(12) United States Patent
Chakrabarty et al.

(10) Patent No.: US 9,222,929 B2
(45) Date of Patent: Dec. 29, 2015

(54) SOLVENT SURVEILLANCE IN SOLVENT-BASED HEAVY OIL RECOVERY PROCESSES

(75) Inventors: Tapantosh Chakrabarty, Calgary (CA);
Scott E. Hommema, Lagos (NG);
Joseph L. Feimer, Bright's Grove (CA)

(73) Assignee: ExxonMobil Upstream Research Company, Houston, TX (US)

( * ) Notice: Subject to any disclaimer, the term of this patent is extended or adjusted under 35 U.S.C. 154(b) by 792 days.

(21) Appl. No.: 13/509,975

(22) PCT Filed: Nov. 10, 2010

(86) PCT No.: PCT/US2010/056229
§ 371 (c)(1),
(2), (4) Date: Aug. 27, 2012

(87) PCT Pub. No.: WO2011/071651
PCT Pub. Date: Jun. 16, 2011

(65) Prior Publication Data
US 2012/0305264 A1    Dec. 6, 2012

Related U.S. Application Data

(60) Provisional application No. 61/267,119, filed on Dec. 7, 2009.

(51) Int. Cl.
*E21B 43/34* (2006.01)
*E21B 43/40* (2006.01)
*G01N 33/28* (2006.01)

(52) U.S. Cl.
CPC .................................. *G01N 33/2823* (2013.01)

(58) Field of Classification Search
CPC ....... E21B 43/255; E21B 43/34; E21B 43/16; E21B 43/40; E21B 43/168; C09K 8/58; C09K 8/592; C09K 8/594
See application file for complete search history.

(56) References Cited

U.S. PATENT DOCUMENTS

| 3,946,810 A | 3/1976 | Barry |
| 3,948,755 A | 4/1976 | McCollum et al. |

(Continued)

FOREIGN PATENT DOCUMENTS

| CA | 940853 | 1/1974 |
| CA | 2075108 | 1/1994 |

(Continued)

OTHER PUBLICATIONS

Tharanivasan, A.K., et al (2009), "Measurement and Modeling of Asphaltene Precipitation from Crude Oil Blends", *Energy & Fuels*, 23, 3971-3980.

(Continued)

*Primary Examiner* — Shane Bomar
*Assistant Examiner* — Kipp Wallace
(74) *Attorney, Agent, or Firm* — ExxonMobil Upstream Research-Law Department

(57) ABSTRACT

The present disclosure relates to solvent surveillance in heavy oil production. A method includes the steps of measuring an amount of a native bitumen marker (NBM) in a heavy oil, measuring an amount of the NBM in a recovery-aid solvent, measuring an amount of the NBM in a blend including the heavy oil and the recovery-aid solvent, and applying a blending model to determine a fraction of the recovery-aid solvent in the blend.

25 Claims, 11 Drawing Sheets

(56) References Cited

U.S. PATENT DOCUMENTS

| | | | | |
|---|---|---|---|---|
| 4,134,012 | A | 1/1979 | Smallbone et al. | |
| 4,293,035 | A * | 10/1981 | Fitch | 166/401 |
| 4,676,889 | A | 6/1987 | Hsieh et al. | |
| 4,843,247 | A | 6/1989 | Yamazoe et al. | |
| 5,236,577 | A | 8/1993 | Tipman et al. | |
| 5,274,572 | A | 12/1993 | O'Neill et al. | |
| 5,607,016 | A | 3/1997 | Butler | |
| 5,781,430 | A | 7/1998 | Tsai | |
| 5,876,592 | A | 3/1999 | Tipman et al. | |
| 5,913,022 | A | 6/1999 | Tinaztepe et al. | |
| 5,920,718 | A | 7/1999 | Uczekaj et al. | |
| 5,968,349 | A | 10/1999 | Duyvesteyn et al. | |
| 6,007,709 | A | 12/1999 | Duyvesteyn et al. | |
| 6,028,819 | A | 2/2000 | Mullarkey et al. | |
| 6,074,558 | A | 6/2000 | Duyvesteyn et al. | |
| 6,182,014 | B1 | 1/2001 | Kenyon et al. | |
| 6,191,787 | B1 | 2/2001 | Lu et al. | |
| 6,195,092 | B1 | 2/2001 | Dhond et al. | |
| 6,214,213 | B1 | 4/2001 | Tipman et al. | |
| 6,275,775 | B1 | 8/2001 | Baco et al. | |
| 6,318,464 | B1 | 11/2001 | Mokrys | |
| 6,323,679 | B1 | 11/2001 | Robertson et al. | |
| 6,358,403 | B1 | 3/2002 | Brown et al. | |
| 6,358,404 | B1 | 3/2002 | Brown et al. | |
| 6,374,252 | B1 | 4/2002 | Althoff et al. | |
| 6,401,081 | B1 | 6/2002 | Montgomery et al. | |
| 6,405,799 | B1 * | 6/2002 | Vallejos et al. | 166/263 |
| 6,411,922 | B1 | 6/2002 | Clark et al. | |
| 6,498,988 | B1 | 12/2002 | Robert et al. | |
| 6,678,642 | B1 | 1/2004 | Budge | |
| 6,712,215 | B2 | 3/2004 | Scheybeler | |
| 6,731,994 | B2 | 5/2004 | Heching et al. | |
| 6,731,998 | B2 | 5/2004 | Walser et al. | |
| 6,800,116 | B2 | 10/2004 | Stevens et al. | |
| 6,829,570 | B1 | 12/2004 | Thambynayagam et al. | |
| 6,910,001 | B2 | 6/2005 | Hammersley et al. | |
| 6,934,931 | B2 | 8/2005 | Plummer et al. | |
| 6,980,935 | B2 | 12/2005 | Lu et al. | |
| 6,980,940 | B1 | 12/2005 | Gurpinar et al. | |
| 6,996,803 | B2 | 2/2006 | Sakamoto et al. | |
| 7,067,811 | B2 | 6/2006 | Long et al. | |
| 7,141,162 | B2 | 11/2006 | Garner et al. | |
| 7,296,274 | B2 | 11/2007 | Cohen et al. | |
| 7,376,472 | B2 | 5/2008 | Wojsznis et al. | |
| 7,451,066 | B2 | 11/2008 | Edwards et al. | |
| 7,478,024 | B2 | 1/2009 | Gurpinar et al. | |
| 7,499,841 | B2 | 3/2009 | Hoffman | |
| 7,516,446 | B2 | 4/2009 | Choi et al. | |
| 7,546,578 | B2 | 6/2009 | Yang | |
| 2003/0015321 | A1 | 1/2003 | Lim et al. | |
| 2003/0015458 | A1 * | 1/2003 | Nenniger et al. | 208/428 |
| 2003/0018490 | A1 | 1/2003 | Magers et al. | |
| 2003/0125818 | A1 | 7/2003 | Johnson | |
| 2003/0139907 | A1 | 7/2003 | McCarthy | |
| 2004/0054564 | A1 | 3/2004 | Fonseca et al. | |
| 2004/0084623 | A1 * | 5/2004 | Long et al. | 250/339.12 |
| 2004/0111428 | A1 | 6/2004 | Rajan et al. | |
| 2005/0027559 | A1 | 2/2005 | Rajan et al. | |
| 2005/0150844 | A1 | 7/2005 | Hyndman et al. | |
| 2005/0263437 | A1 | 12/2005 | Howdeshell | |
| 2006/0111903 | A1 | 5/2006 | Kemmochi et al. | |
| 2006/0113218 | A1 | 6/2006 | Hart et al. | |
| 2006/0138036 | A1 | 6/2006 | Garner et al. | |
| 2006/0138055 | A1 | 6/2006 | Garner et al. | |
| 2006/0196812 | A1 | 9/2006 | Beetge et al. | |
| 2006/0249439 | A1 | 11/2006 | Garner et al. | |
| 2006/0260980 | A1 | 11/2006 | Yeung | |
| 2006/0282243 | A1 | 12/2006 | Childs et al. | |
| 2007/0108098 | A1 | 5/2007 | Flint et al. | |
| 2007/0156377 | A1 | 7/2007 | Gurpinar et al. | |
| 2007/0168057 | A1 | 7/2007 | Blevins et al. | |
| 2007/0168741 | A1 | 7/2007 | Chadha et al. | |
| 2007/0295640 | A1 | 12/2007 | Tan et al. | |
| 2008/0208552 | A1 | 8/2008 | Kumar et al. | |
| 2008/0288226 | A1 | 11/2008 | Gurpinar et al. | |
| 2009/0107890 | A1 * | 4/2009 | Hamad et al. | 208/208 R |
| 2009/0211378 | A1 | 8/2009 | Conquorgood et al. | |
| 2009/0266744 | A1 * | 10/2009 | LaCour | 208/216 R |

FOREIGN PATENT DOCUMENTS

| | | |
|---|---|---|
| CA | 2200899 | 9/1998 |
| CA | 2232929 | 9/1998 |
| CA | 2353109 | 1/2003 |
| CA | 2502943 | 5/2004 |
| CA | 2505411 | 7/2004 |
| CA | 2425840 | 10/2004 |
| CA | 2435113 | 1/2005 |
| CA | 2493677 | 6/2005 |
| CA | 2455011 | 7/2005 |
| CA | 2490734 | 6/2006 |
| CA | 2502329 | 9/2006 |
| CA | 2521248 | 3/2007 |
| WO | WO 99/33936 | 7/1999 |
| WO | WO 2009/048701 | 4/2009 |

OTHER PUBLICATIONS

PCT/US2010/56229 International search Report and Written Opinion.

* cited by examiner

SOLVENT SURVEILLANCE IN SOLVENT-BASED HEAVY OIL RECOVERY PROCESSES

CROSS-REFERENCE TO RELATED APPLICATION

This application is the National Stage of International Application No. PCT/US2010/056229, filed 10 Nov. 2010, which claims the benefit of U.S. Provisional Patent Application 61/267,119 filed 7 Dec. 2009 entitled SOLVENT SURVEILLANCE IN SOLVENT-BASED HEAVY OIL RECOVERY PROCESSES, the entirety of which is incorporated herein by reference in its entirety.

FIELD

Embodiments of the invention relate to solvent surveillance. More particularly, improved solvent surveillance methods for solvent-based heavy oil recovery processes are provided.

BACKGROUND

This section is intended to introduce various aspects of the art, which may be associated with exemplary embodiments of the presently disclosed invention. This discussion is believed to assist in providing a framework to facilitate a better understanding of particular aspects of the presently disclosed invention. Accordingly, it should be understood that this section should be read in this light, and not necessarily as admissions of prior art.

Various methods are used in the recovery of deeply buried heavy oil or bitumen deposits within oil-sands reservoirs. In situ heavy oil or bitumen recovery techniques are applied to indigenous resource that cannot be mined economically because of the depth of the overburden. It is recognized that in situ methods disturb considerably less land and therefore require less land-reclamation activity than mining projects. In general, the focus of in situ heavy oil or bitumen recovery processes is to reduce the viscosity of the heavy oil or bitumen to enable it to be produced from a well and transported by pipeline or other means. One method of reducing the viscosity of the heavy oil or bitumen is to introduce a recovery-aid solvent, such as by reservoir injection, into the heavy oil or bitumen. Such a process may be referred to as a solvent-based recovery process (such as Cyclic Solvent Process, Hot Solvent Process, and Vapor Extraction). A second method of reducing viscosity of the heavy oil or bitumen is to introduce the recovery-aid solvent along with other viscosity reducing agents including but not limited to, steam, hot water or hot gases. Such a process may also be referred to as a solvent-based recovery process (such as Expanding Solvent Steam Assisted Gravity Drainage, Solvent Assisted Steam Assisted Gravity Drainage, Liquid Addition to Steam for Enhanced Recovery, and Solvent Steam Assisted Vapor Extraction).

Upon recovery, the heavy oil/bitumen is generally in the form of an emulsion containing the recovery-aid solvent as well as water. To separate the water from the emulsion, a separation-aid solvent is generally added to facilitate the separation of the water through density and viscosity reduction.

One challenge in any solvent-based recovery process is the accurate determination of the amount (e.g., mass, volume, percentage, and the like) of the recovery-aid solvent that is recovered from the reservoir along with the heavy oil/bitumen. An accurate accounting of the recovery-aid solvent may be beneficial, for example, in maintaining desirable environmental conditions, determining the efficiency of the recovery process, determining the appropriate processing of the emulsion, obtaining regulatory approval to develop a heavy oil/bitumen project, and/or assessing the economic feasibility of a given solvent-based recovery process.

Conventional methods of measurement of recovery-aid solvent rely on gas chromatography (GC), Fourier Transform Infrared spectroscopy (FTIR), thermogravimetry (TG), solvent evaporation, density measurements, or viscosity measurements. Because of inaccuracies and impreciseness of the other methods, GC is the most preferred conventional method. However, the GC method is not accurate because the boiling ranges of the heavy components in the solvent overlap with the light components in the recovered crude. Also, the reliability of the GC process may not be optimal due to the potential for contamination of the GC column by non-eluted heavy oil/bitumen.

As such, there is still a substantial need for an improved system and method for determining the amount of a recovery-aid solvent in the recovery-aid solvent diluted heavy oil/bitumen that is produced from a reservoir.

SUMMARY

One embodiment discloses a method of solvent surveillance. The method comprises the steps of measuring an amount of a native bitumen marker (NBM) in a heavy oil, measuring an amount of the NBM in a recovery-aid solvent, measuring an amount of the NBM in a blend of at least the heavy oil and the recovery-aid solvent, and applying a blending model to determine the fraction of the recovery-aid solvent in the blend.

In at least one exemplary embodiment, the blending model is at least partially described by formula: the fraction of the recovery-aid solvent in the blend=(NBMo−NBMb)/(NBMo−NBMras); wherein NBMo is the amount of the NBM in the heavy oil, NBMb is the amount of the NBM in the blend, and NBMras is the amount of the NBM in the recovery-aid solvent.

In the above formula, the amount of NBM in the blend is on a separation-aid solvent free basis. However, in one or more embodiments, a separation-aid solvent, such as toluene, may be added to the sampled emulsion to remove water, leaving a hydrocarbon blend composed primarily of heavy oil/bitumen, separation-aid solvent and recovery-aid solvent. This hydrocarbon sample containing the separation-aid solvent may then be analyzed for the recovery-aid solvent. In such an embodiment, the amount of NBM in the blend may be measured in the presence of the separation-aid solvent. However, the NBM in the heavy oil and the recovery-aid solvent are generally measured separately and reported on a separation-aid solvent free basis. As such, the method may include the step of modifying the blending formula to include the fraction of a separation-aid solvent in the blend, which is generally known. The blending model may then be at least partially described by the formula: the fraction of the recovery-aid solvent in the blend (on a separation-aid solvent free basis)= [NBMo−NBMb*(1/(1−SASFb))]/(NBMo−NBMras); wherein NBMo is the amount of the NBM in the heavy oil, NBMb is the amount of the NBM in the blend including the separation-aid solvent, NBMras is the amount of the NBM in the recovery-aid solvent, SASFb is the fraction of the separation-aid solvent in the blend.

Another embodiment discloses a heavy oil production method comprising the steps of injecting a recovery-aid solvent into a heavy oil formation via, for example, a reservoir and using, for example, a solvent-based heavy oil production process to form an initial blend of the recovery-aid solvent and heavy oil; producing (i.e., recovering) the initial blend from the reservoir; recovering, in a solvent recovery process, at least a portion of the recovery-aid solvent from the initial blend to form a partially recovered blend; and applying a solvent surveillance method to the partially recovered blend. One or more embodiments of the heavy oil production method may apply one or more of the solvent surveillance methods and/or blending models previously described in this section.

BRIEF DESCRIPTION OF THE DRAWINGS

The foregoing and other advantages of the present invention may become apparent upon reviewing the following detailed description and drawings of non-limiting examples of embodiments in which.

DETAILED DESCRIPTION

Figure 1A:
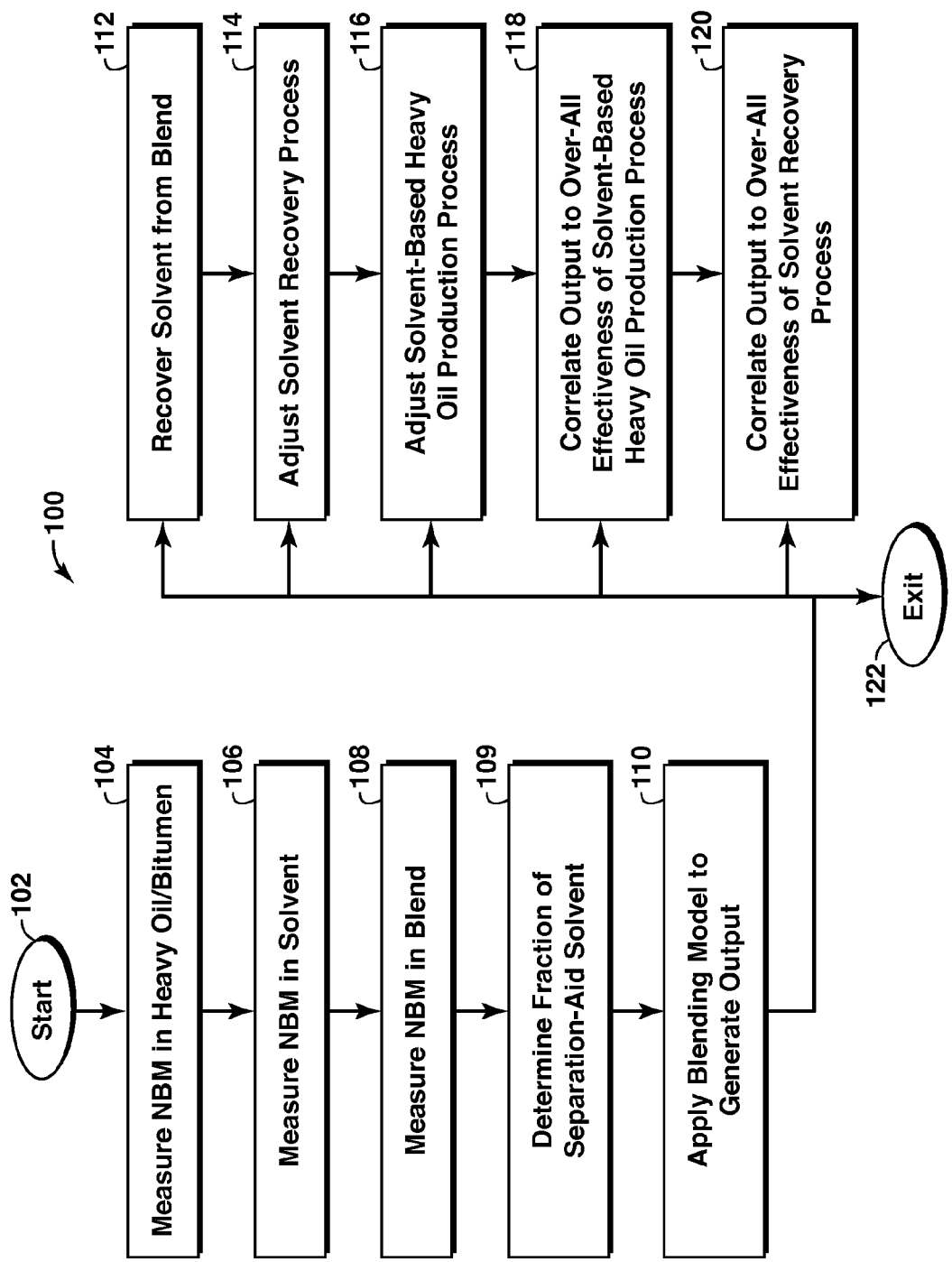
FIG. 1A is a flow diagram of a method of solvent surveillance according to an embodiment of the present invention.

In the following detailed description section, some specific embodiments of the present invention are described in connection with preferred, alternative, and exemplary embodiments. However, to the extent that the following description is specific to a particular embodiment or a particular use of the present invention, this is intended to be for illustrative purposes only and simply provides a description of the particular embodiments. Accordingly, the invention is not limited to the particular embodiments described below, but rather, it includes all alternatives, modifications, and equivalents falling within the true spirit and scope of the appended claims.

Definitions

Various terms as used herein are defined below. To the extent a term used in a claim is not defined below, it should be given the broadest definition persons in the pertinent art have given that term.

As used herein, the "a" or "an" entity refers to one or more of that entity. As such, the terms "a" (or "an"), "one or more", and "at least one" can be used interchangeably herein unless a limit is specifically stated.

As used herein, the term "heavy oil" refers to hydrocarbon fluids that are highly viscous at ambient conditions (e.g., 15 deg. C and 1 atm pressure). Heavy oil may include carbon and hydrogen, as well as smaller concentrations of sulfur, oxygen, and/or nitrogen. As used in this application, heavy oil may include any hydrocarbon fluid having API gravity lower than about 20 degrees such as, but not limited to, bitumen, de-asphalted bitumen, tar and/or asphalt.

As used herein, the term "bitumen" refers to a non-crystalline solid or viscous hydrocarbon material that is substantially soluble in carbon disulfide, toluene, xylene or methylene chloride. The terms bitumen and heavy oil are used interchangeably throughout this disclosure.

As used herein, the term "recovery-aid solvent" refers to alkanes, such as methane, ethane, propane, butane, pentane, hexane, heptane and other higher molecular weight alkanes, alkenes, naphthenes, aromatics or mixtures thereof, which when blended with bitumen reduces its viscosity. Recovery-aid solvent may also include gas plant condensates, which are mixtures of alkanes, alkenes, naphthenes and aromatics.

As used herein, the term "NBM" means native bitumen markers, which are any measurable elements (e.g., S, V or Ni) or components (such as asphaltenes, CCR or MCR) that are naturally present in bitumen in substantial amounts and are not present in substantial amounts in solvent.

As used herein, the term "asphaltenes" means components of bitumen that precipitate out in the presence of substantial amount of solvents, such as n-pentane, n-hexane or n-heptane, and are described as nC5-asphaltenes, nC6-asphaltenes or nC7-asphaltenes, respectively.

As used herein, the term "MCR" means the microcarbon residue as determined by ASTM D4530.

As used herein, the term "CCR" means Conradson carbon reside as determined by ASTM D189.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "containing," "contains," and "contain" have the same open-ended meaning as "comprising," "comprises," and "comprise."

As used herein, the terms "having," "has," and "have" have the same open-ended meaning as "comprising," "comprises," and "comprise."

As used herein, the terms "including," "includes," and "include" have the same open-ended meaning as "comprising," "comprises," and "comprise."

As used herein, the term "solvent-based production process" means a process that uses recovery-aid solvent to produce heavy oil as a heavy oil-solvent blend.

As used herein, the term "solvent recovery process" means a process that recovers solvent, at least partially, from a heavy oil-solvent blend.

As used herein, the term "blend" means a mixture of heavy oil and recovery-aid solvent which may contain free water and/or emulsified water.

Description

With reference to the figures, wherein like reference numbers indicate like elements, embodiments of the present invention are described for providing improved surveillance of a solvent (i.e., a recovery-aid solvent) used in connection with recovery of heavy oil. Unless specifically stated otherwise, subsequent uses of the term "solvent" refer to a recovery-aid solvent; as opposed to a separation-aid solvent.

More specifically, one or more native bitumen markers (NBMs) are measured and a blending model is applied to determine a fraction (i.e., amount) of a solvent in a blend of heavy oil and solvent. One or more embodiments of the present invention may also provide for the adjustment of one or more steps involved in the recovery or post recovery processing of the heavy oil. As used in this application, the term "heavy oil" will be used interchangeably with "bitumen" and will refer to any appropriate hydrocarbon material that satisfies either definition, as specified in the Definitions section of this application, and/or would be recognized as a heavy oil or bitumen by one of ordinary skill in the art. For example, the term heavy-oil includes partially and/or completely de-asphalted bitumen such as may be produced through solvent-based extraction operations. The partially or completely de-asphalted bitumen, which may be referred to as maltene, may be a result of asphaltene precipitation in the formation or wellbore and/or a result of operations on the surface. In addition, the measured NBM may be any component suitable for distinguishing the heavy oil from solvent. Preferably, the NBM is a component that is substantially present in heavy oil and substantially lacking in the solvent of interest; for example sulfur (S), nickel (Ni), vanadium (V), chromium (Cr), micro-carbon residue (MCR), Conradson carbon residue (CCR), nC5-asphaltenes, nC6-asphaltenes or nC7-asphaltenes.

Referring to FIG. 1A, a flow diagram of a method 100 of solvent surveillance according to an embodiment of the present invention is shown. The method 100 generally includes a plurality of blocks or steps that may be performed serially. As will be appreciated by one of ordinary skill in the art, the order of the steps shown in FIG. 1A is exemplary and the order of one or more steps may be modified within the spirit and scope of the present invention. Additionally, the steps of the method 100 may be performed in at least one non-serial (or non-sequential) order, and one or more steps may be omitted to meet the design criteria of a particular application. Step 102 represents an entry point into the method 100.

At step 104, the NBM in the heavy oil is measured. In at least one embodiment, one or more samples of the heavy oil are extracted from one or more wells associated with the heavy oil recovery site. In such an embodiment, the NBM of the heavy oil may be determined by analyzing the one or more samples. Similarly, at steps 106 and 108, the NBM of the solvent and the blend (e.g., the heavy oil and solvent blend which has been extracted from a reservoir), respectively, are measured.

As is well understood, the asphaltene components of the heavy oil in the reservoir are susceptible to precipitation depending on the nature and quantity of solvent injected into the reservoir. When such asphaltene precipitation does occur, or is prone to occur, it may be difficult to control the degree of precipitation, or the degree to which the heavy oil is de-asphalted. In such implementations, the measurement of the heavy oil NBM may include completely de-asphalting the heavy oil to provide a consistent basis. The heavy oil may be de-asphalted through any conventional techniques implemented either in the formation or on the surface. The NBM of the de-asphalted heavy oil may then be measured to complete step 104. Similarly, in implementations where the produced heavy oil is at least partially de-asphalted, it will be recognized that the NBM of the blend, at step 108, is measured after completely de-asphalting the solvent and heavy oil blend. Accordingly, the heavy oil NBM, at 104, and the blend NBM, at 108, are measured on a consistent basis, either with all of the naturally occurring asphaltene components or with them all removed.

Step 109 represents the optional step of determining a fraction of a separation-aid solvent. This may be done by adding a known amount of the separation-aid solvent to the known amount of the produced emulsion sample, centrifuging the emulsion and then determining the amount of the total hydrocarbon (heavy oil, recovery-aid solvent and separation-aid solvent) separated, and assuming that all the separation-aid solvent is in the total hydrocarbon. Separation-aid solvents will be discussed further in connection with step 110.

While steps 104, 106, and 108 refer to "measurement", it should be appreciated that an amount of a NBM may be determined either directly, such as by direct testing/observation of a sample of the relevant substance, or indirectly, such as by calculation or estimation. In the case of direct testing/observation, any suitable method/apparatus/technology may be used such as one or more of: an X-Ray Fluorescence analyzer (for S, Ni and V), Inductively Coupled Plasma Emission Spectroscopy (ICPES) (for Ni and V), combustion fluorescence (for S), ultraviolet fluorescence (for S), asphaltenes by solvent precipitation, and MCR by pyrolysis in absence of oxygen. Likewise, any appropriate unit of measure may be used such as weight fraction, mole fraction, volume fraction, and parts per million (by volume or weight).

At step 110, an appropriate blending model is applied to the measured NBM values to generate an output which corresponds to the amount of recovery-aid solvent in the blend. In at least one embodiment, the blending model is at least partially described by the formula:

the fraction of the recovery-aid solvent=
  $(NBMo-NBMb)/(NBMo-NBMras)$ where:
NBMo=the amount of a given NBM in the heavy oil
NBMb=the amount of the given NBM in the blend
NBMras=the amount of the given NBM in the recovery-aid solvent In the above formula, each of the amount of NBM in the blend, heavy oil and solvent is expressed on a separation-aid solvent free basis. In practice, a separation-aid solvent, such as toluene, may be added to the blend to remove water. As such, it may be necessary and/or advantageous to measure (e.g., at step 108) the amount of NBM in the blend containing the separation-aid solvent. The NBM in the heavy oil and the recovery-aid solvent may be measured separately on a separation-aid solvent free basis. The blending model for determining the fraction of the recovery-aid solvent in the blend when separation-aid solvent is present may be at least partially described by the formula:

the fraction of the recovery-aid solvent in the blend on
  a separation-aid solvent free basis=$[NBMo-NBMb*(1/(1-SASFb))]/(NBMo-NBMras)$ where:
NBMo=the amount of a given NBM in the heavy oil
NBMb=the amount of the given NBM in the blend including the separation-aid solvent
NBMras=the amount of the given NBM in the recovery-aid solvent
SASFb=the fraction of the separation-aid solvent in the blend While the above exemplary formula can be used when accounting for the separation-aid solvent, any appropriate blending model may be implemented to satisfy the design criteria of a particular embodiment. For example, similar modifications of the formula may be implemented to account for de-asphalted heavy oil, as discussed above. Furthermore, one or more specific embodiments of the present invention may include one or more iterations of the steps 104, 106, 108, 109 and/or 110. In such an embodiment, each iteration may measure a different NBM; that is, a different NBM may be selected for each iteration. Such an iterative process may increase the accuracy of the determined amount of solvent.

Similarly, a plurality of NBMs may be used to increase the accuracy of the determination of the solvent fraction.

As illustrated in FIG. 1A, the method 100 may, depending on the particular application, include one or more additional steps (e.g., steps 112, 114, 116, 118, and/or 120). For example, at least one embodiment may include the step of recovering, in a solvent recovery process, at least a portion of the solvent from the blend of heavy oil and solvent (i.e., step 112). Similarly, optional step 114 includes adjusting at least one step in a solvent recovery process (such as the solvent recovery process of step 112) in response to the output of step 110; optional step 116 includes adjusting at least one step in a corresponding solvent-based heavy oil production process in response to the output of step 110; optional step 118 includes correlating the output of step 110 to an overall effectiveness of a solvent-based heavy oil production process (such as the process of step 116); and optional step 120 includes correlating (i.e., relating) the output of step 110 to an overall effectiveness of a solvent recovery process (such as the process of step 112).

Step 122 represents an exit point out of the method 100.

Figure 1B:
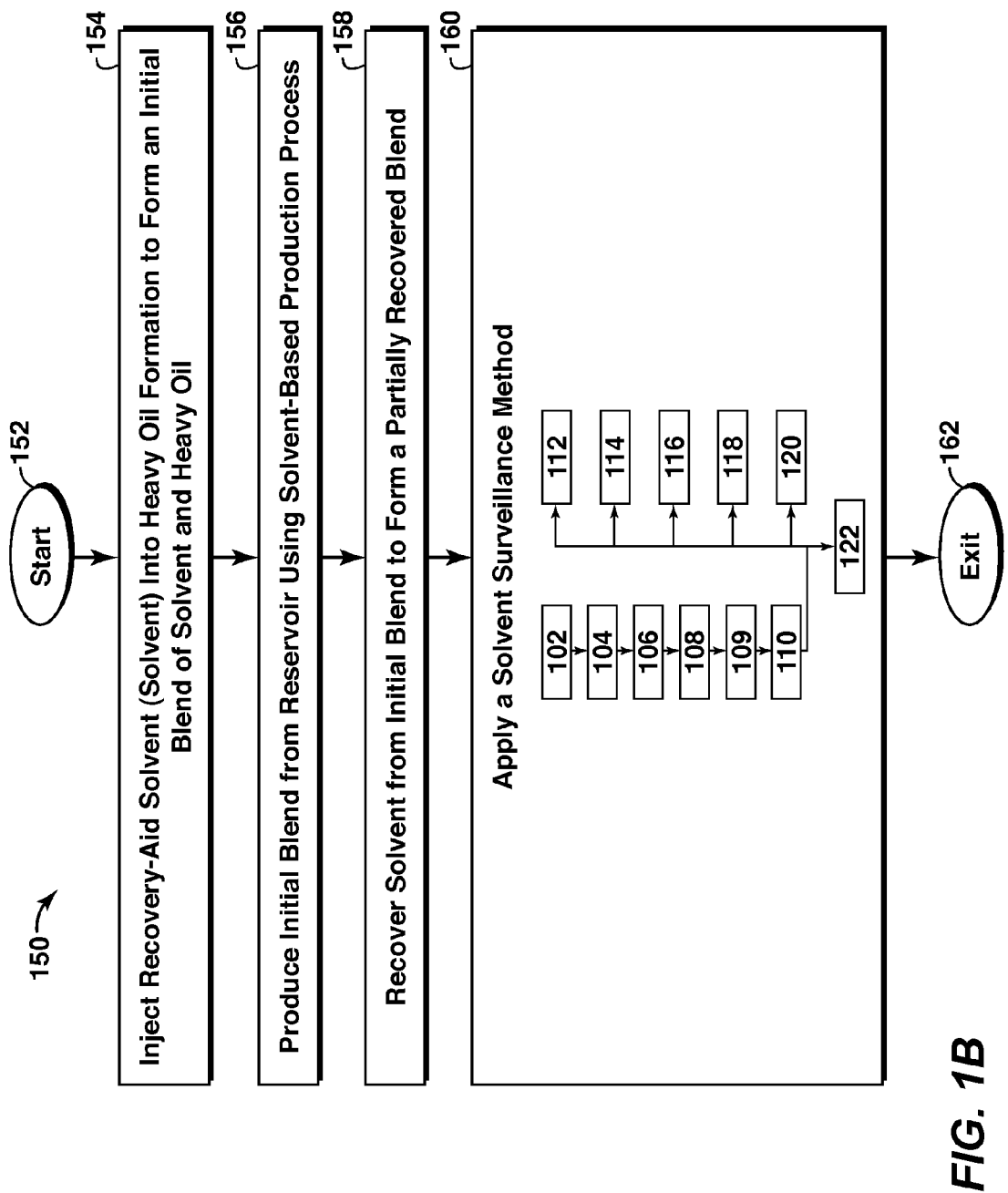
FIG. 1B is a flow diagram of a heavy oil production method according to an embodiment of the present invention.

Referring now to FIG. 1B, a flow diagram of a heavy oil production method 150 according to an embodiment of the present invention is shown. Like the method 100, the method 150 generally includes a plurality of blocks or steps that may be performed serially. As will be appreciated by one of ordinary skill in the art, the order of the steps shown in FIG. 1B is exemplary and the order of one or more steps may be modified within the spirit and scope of the present invention. Additionally, the steps of the method 150 may be performed in at least one non-serial (or non-sequential) order, and one or more steps may be omitted to meet the design criteria of a particular application. Step 152 represents is an entry point into the method 150.

At step 154 a recovery-aid solvent is injected into the heavy oil reservoir to form an initial blend that may contain water either as free water and/or emulsified water. The initial blend is then recovered (i.e., produced), at step 156, from a corresponding reservoir using a solvent-based production process such as: (i) Expanding Solvent Steam Assisted Gravity Drainage ("ES-SAGD"); (ii) Solvent Assisted Steam Assisted Gravity Drainage ("SA-SAGD"); (iii) Liquid Addition to Steam for Enhanced Recovery ("LASER"); Vapor Extraction (VAPEX), Combined Vapor and Steam Recovery ("SAVEX"); Cyclic Solvent Process ("CSP"), Hot Solvent Process; or any combination thereof. As discussed above, the initial blend may be de-asphalted through a variety of techniques to complete any asphaltene precipitation that may have begun during the recovery. Step 158 includes recovering, in a solvent recovery process, at least a portion of the solvent from the initial blend to form a partially recovered blend. As illustrated at step 160, a solvent surveillance method, such as the method 100 of FIG. 1A, may be advantageously implemented in connection with the partially recovered blend of step 158.

Step 162 represents an exit point out of the method 150.

Figure 2:
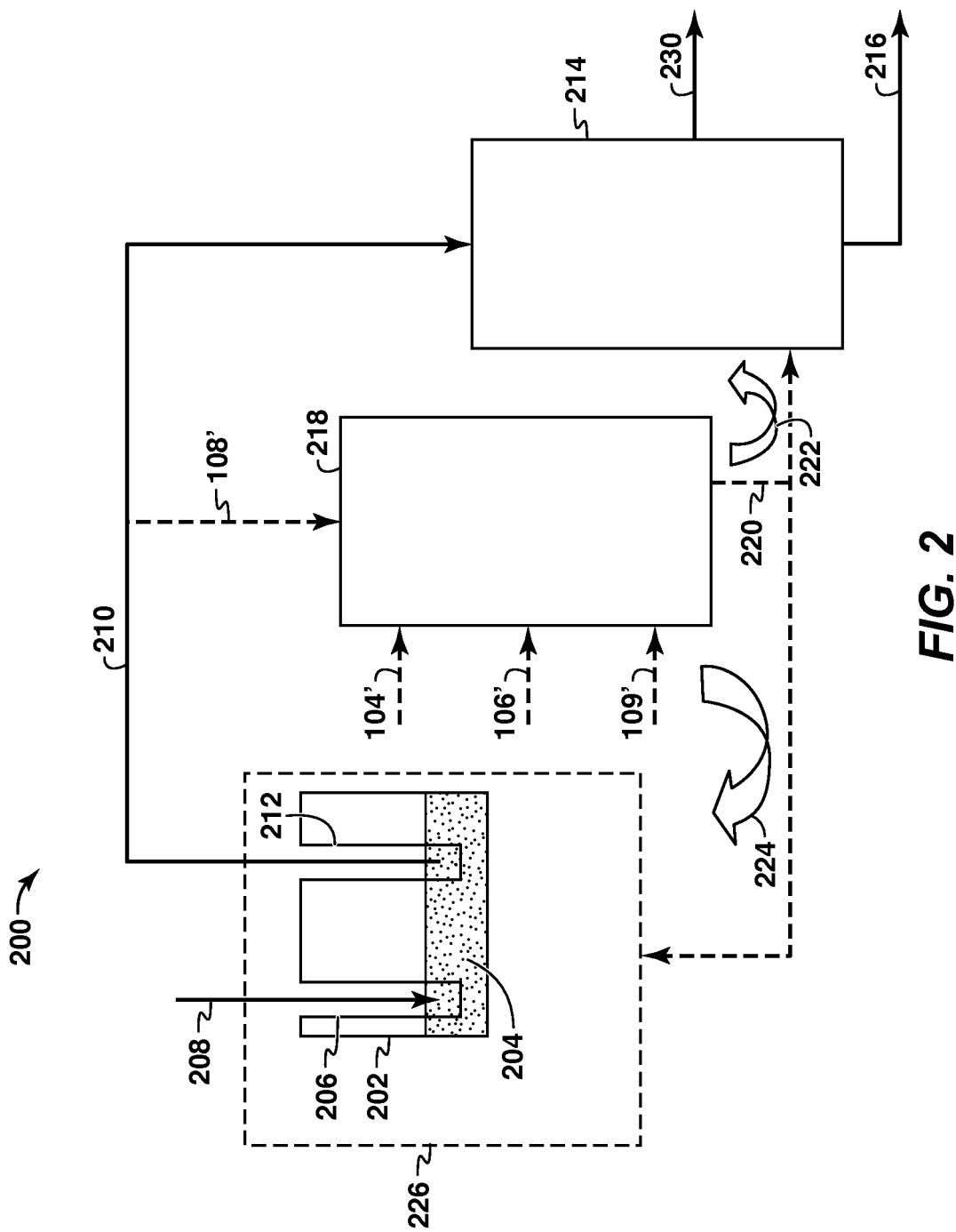
FIG. 2 illustrates a solvent-based heavy oil/bitumen production process with solvent surveillance in accordance with a first embodiment of the invention.

Referring to FIG. 2, a block diagram 200 of a solvent-based heavy oil production process 226 with solvent surveillance in accordance with an embodiment of the invention is provided. Element 202 represents a heavy oil reservoir. In at least one embodiment, an injection well 206 is drilled into the reservoir 202. The injection well 206 generally provides a mechanism for injecting substances, such as solvents 208 and/or steam (not shown), into the reservoir 202 for the purpose of reducing the viscosity of the heavy oil 204 within the reservoir 202. The viscosity-reduced blend (i.e., initial blend) 210 of heavy oil 204 and solvent 208 may then be extracted using any appropriate process such as one or more of the solvent-based production processes previously discussed in connection with step 156 of FIG. 1B. The recovery process 226 generally includes a production well 212.

The blend 210, or a portion thereof, may then be processed using a solvent recovery process 214 to produce a partially recovered blend 216 using any appropriate mechanism such as: (i) distillation, (ii) fractionation, (iii) evaporation, (iv) membrane separation, or any combination thereof. The partially recovered blend 216 may be characterized by a reduction in the amount of solvent 208 as compared to the initial blend 210. As such, the solvent recovery process 214 acts to recover (i.e., separate, remove, etc.) at least a portion of the solvent 208 from the blend 210. Element 230 generally represents the recovered solvent.

As further illustrated in FIG. 2, a solvent surveillance method 218, such as the method 100 described in connection with FIG. 1A, may be performed on the blend 210. The method 218 may take the NBM of the heavy oil 204, the NBM of the solvent 208 and the NBM of the blend 210 as inputs 104', 106' and 108' respectively. In some implementations, as previously discussed, measuring the NBM of the heavy oil 204 and the NBM of the blend 210 may include measuring the NBM of the de-asphalted heavy oil and blend. Optionally, the method 218 may take the fraction of a separation-aid solvent as input 109'. In at least one embodiment, the output 220, corresponding to the amount/fraction of solvent 208 in the blend 210, of the solvent surveillance method 218 may be used to adjust at least one step in the solvent recovery process 214. As such, the output 220 may be used in connection with a feed-forward control loop 222 to the solvent recovery process 214. Similarly, an embodiment of the present invention may use the output 220 to adjust at least one step in the heavy oil production process 226. As such, the output 220 may be used in connection with a feedback control loop 224. In yet another embodiment, the output 220 may be correlated to an overall effectiveness of the solvent-based heavy oil production process 226.

Figure 3:
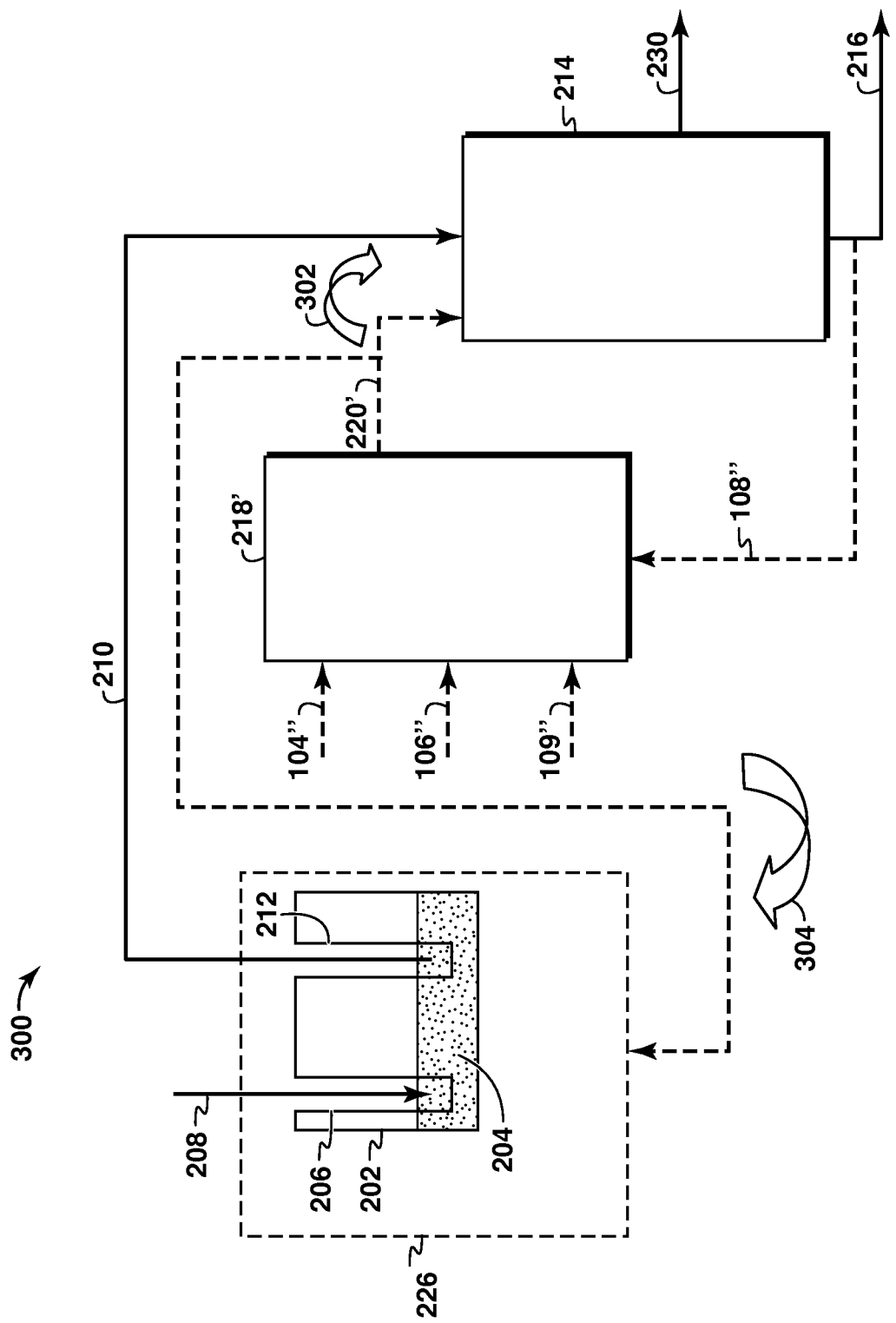
FIG. 3 illustrates another solvent-based heavy oil/bitumen production process with solvent surveillance in accordance with a second embodiment of the invention.

Turning now to FIG. 3, a block diagram 300 illustrating another solvent-based heavy oil production process 226' with solvent surveillance that may be implemented in connection with the present invention is shown. The solvent surveillance method 218' generally takes the NBM of the heavy oil 204, the NBM of the solvent 208 and the NBM of the partially recovered blend 216 as inputs 104", 106" and 108" respectively. Optionally, the method 218' may take the fraction of the separation-aid solvent as input 109". Accordingly, the process 300 may be implemented similarly to the process 200 of FIG. 2 with the exception that the solvent surveillance method 218', such as the method 100, is performed on the partially recovered blend 216 instead of the initial blend 210.

In accordance with at least one embodiment of FIG. 3, the output 220', corresponding to the amount/fraction of solvent in the partially recovered blend 216, may be used to adjust at least one step in the solvent recovery process 214. As such, the output 220' may be used in connection with a first feedback control loop 302 to the solvent recovery process 214 and/or correlated to an overall effectiveness of the solvent recovery process 214. Similarly, one or more embodiments may use the output 220' to adjust at least one step in the heavy oil production process 226'. As such, the output 220' may be used in connection with a second feedback control loop 304 and/or correlated to an overall effectiveness of the heavy oil production process 226'.

While FIGS. 2 and 3 illustrate implementations where the solvent surveillance is applied to either the produced blend 210 or the partially recovered blend 216, the solvent surveillance methods and systems described herein may be applied to any heavy oil stream or combinations of heavy oil streams. For example, some implementations may apply the present solvent surveillance methods and systems to both the produced blend 210 and the partially recovered blend 216 and provide feedback and/or feedforward control based on either or both streams. Such an implementation may inform the operator regarding the effective recovery of solvent from the formation and the effectiveness of the solvent recovery process 214. In implementations where the partially recovered blend 216 is sent for further processing, the present solvent surveillance systems and methods may be applied to still further downstream processes to determine the effectiveness of later solvent recovery efforts.

Figure 4:
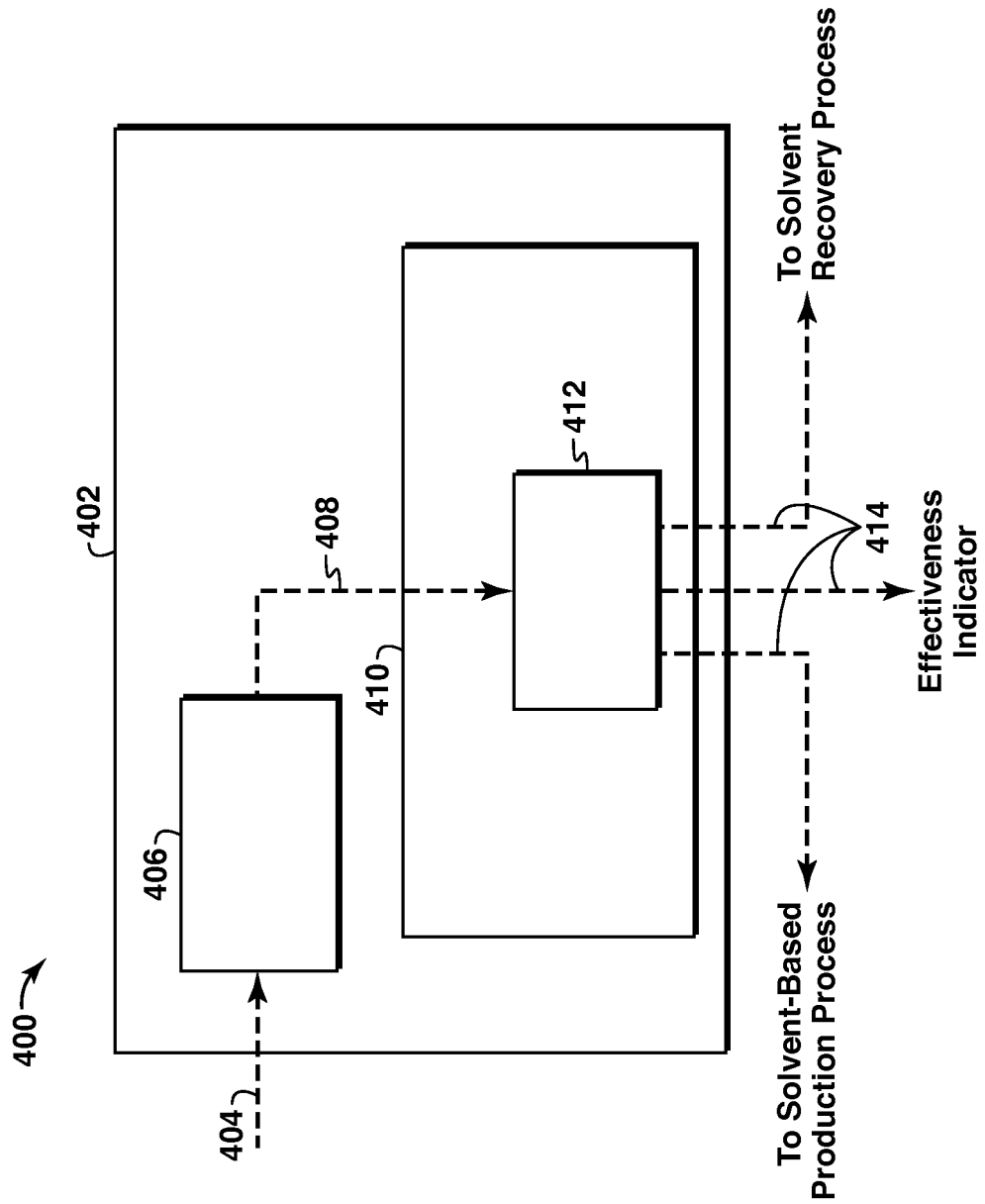
FIG. 4 illustrates an automatic control system for solvent surveillance according to an embodiment of the invention.

Referring to FIG. 4, an automatic control system 400 for solvent surveillance according to an embodiment of the present invention is shown. The system 400 generally includes a control module (i.e., controller) 402 and may be advantageously implemented in connection with the method 100 of FIG. 1A, the method 150 of FIG. 1B, the embodiment of FIG. 2, the embodiment of FIG. 3 and/or any appropriate system and/or method to meet the design criteria of a particular application. The controller 402 may be a computer such as the computer environment discussed in connection with FIG. 5 (below), an application specific integrated circuit ("ASIC"), an electronic circuit, a processor (shared, dedicated, or group) and memory that execute one or more software or firmware programs, a combinational logic circuit, and/or other suitable component(s) that provides the described functionality. It is contemplated that all or part of the functionality of the components in the controller 402 may be incorporated into a single module, such as shown in FIG. 4. Alternatively, one or more functions of the controller 402 may be distributed among a plurality of modules (not shown).

The controller 402 may receive input signals (i.e., inputs) 404 using any appropriate mechanism to suit the design criteria of a particular application. Each input 404 generally represents one or more physical characteristic of real world materials and may, for example, represent the amount of NBM in a corresponding (i) heavy oil, (ii) solvent, or (iii) blend (initial, partially recovered, or otherwise). In at least one embodiment, the input 404 may optionally represent the determined fraction of a separation-aid solvent in a blend.

As illustrated in FIG. 4, the controller 402 may apply a blending model 406, such as a blending model described in connection with step 110 of FIG. 1A, to the inputs 404 to determine a solvent fraction 408 of a corresponding blend of solvent and heavy oil. It may be appreciated that the solvent fraction 408 represents the real world physical amount/concentration of solvent in the blend.

In at least one embodiment, the controller 402 is in electrical communication with a computer readable medium 410. The computer readable medium 410 may be any appropriate mechanism for storing and retrieving electronic instructions 412 such as a magnetic medium (e.g., a disk or tape); a magneto-optical or optical medium (e.g., a disk); a solid state medium (e.g., a memory card) as well as art-recognized equivalents and successor technologies. In addition, the medium 410 may be physically integrated with the controller 402, as illustrated in FIG. 4, remotely located from the controller 402 (not shown), or a combination thereof. The medium (i.e., media) may include one or more set of instructions 412. Each set of instructions 412 may comprise one or more individual instructions for generating one or more output signals 414 based at least in part on the solvent fraction 408.

As illustrated in FIG. 4, an output signal 414 may be implemented to control at least one step in a solvent recovery process, such as the solvent recovery process 214. Similarly, an output signal 414 may be implemented to control at least one step in a solvent-based heavy oil production process, such as the production processes 226 and/or 226'. In yet another embodiment, an output signal 414 may correlate the determined solvent fraction 408 to an effectiveness of a corresponding solvent-based production process (such as the production processes 226 and/or 226'), a corresponding solvent recovery process (such as the recovery process 214), and/or the like.

Figure 5:
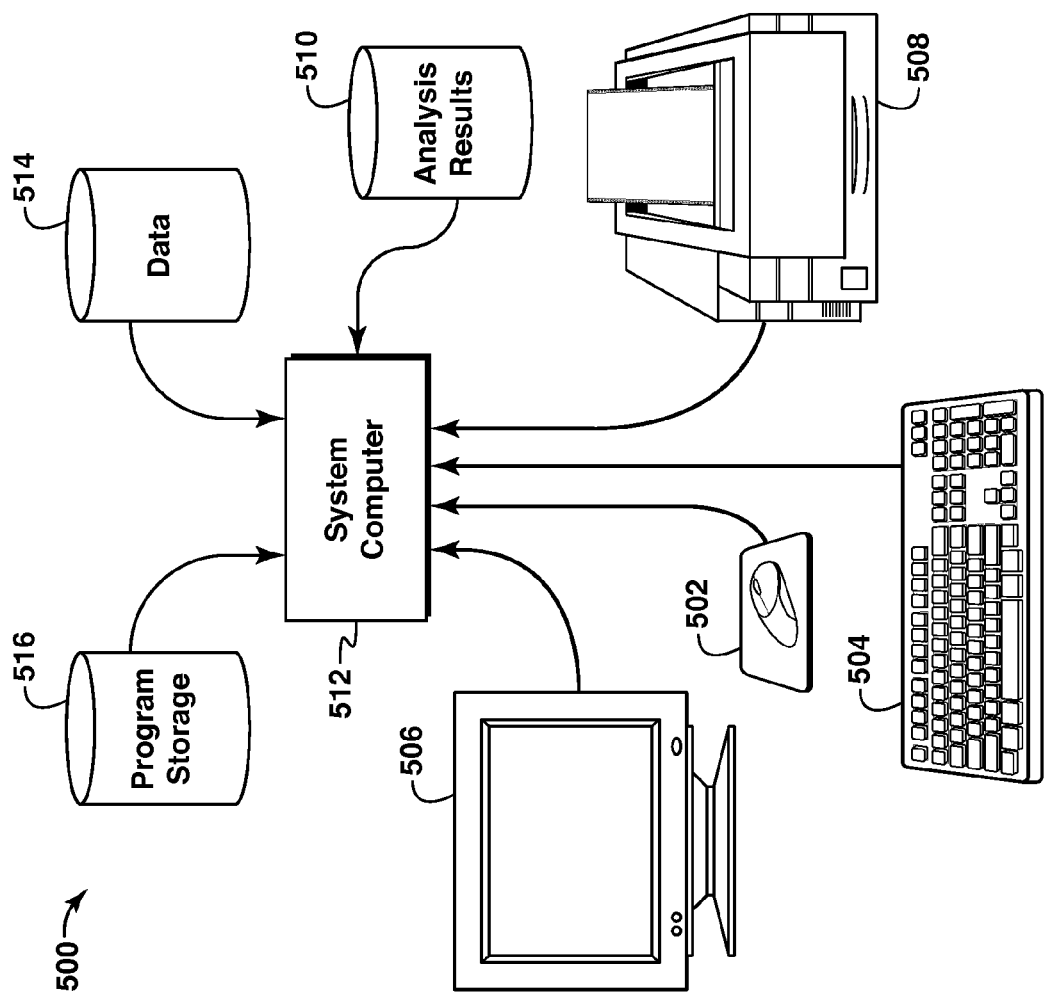
FIG. 5 illustrates a block diagram of a computer environment which may be implemented as part of an embodiment of the present invention.

Referring now to FIG. 5, there is illustrated a block diagram of a computer environment 500 that may be advantageously implemented in connection with the method 100 of FIG. 1A, the method 150 of FIG. 1B, the processes of FIGS. 2 and 3, and/or the controller 402 of FIG. 4. In general, FIG. 5 and the following discussion are intended to provide a brief description of a suitable computing environment 500 in which the various aspects of the claimed subject matter may, if advantageous for a particular application, be implemented.

With reference again to FIG. 5, the exemplary environment 500 may include a system computer 512, which may be implemented as any conventional personal computer or workstation, such as a UNIX-based workstation. The system computer 512 may be in electronic communication with data storage devices 510, 514, and 516 (e.g., disk storage devices) which may be external storage devices, internal storage devices, or a combination of internal and external storage devices. Electronic communication between external storage devices and the system computer 512 may be established via any suitable mechanism such as via a local area network, USB cable, parallel data cable, serial data cable, firewire cable, and/or remote access. Of course, while storage devices 510, 514, and 516 are illustrated as separate devices, a single storage device may be used to store any and all of the corresponding information (e.g., program instructions, data, and results) as desired.

In one embodiment, the input data are stored in storage device 514. The system computer 512 may retrieve the appropriate data from the storage device 514 to perform operations according to program instructions that correspond to the methods described herein. The program instructions may be written in a computer programming language, such as C++, Java and the like. The program instructions may be stored in a computer-readable memory, such as program storage device 516. Of course, the memory medium storing the program instructions may be of any conventional type used for the storage of computer programs, including hard disk drives, floppy disks, CD-ROMs and other optical media, magnetic tape, and the like.

According to an embodiment, the system computer 512 presents output onto graphics display 506, or alternatively via printer 508. The system computer 512 may store the results of the methods described above on storage device 510, for later use and further analysis. The keyboard 504 and the pointing device (e.g., a mouse, trackball, or the like) 502 may be provided with the system computer 512 to enable interactive operation with an operator. The system computer 512 may be located at a data center remote from the corresponding reservoir (such as the reservoir 202 of FIGS. 2 and 3).

Figure 6:
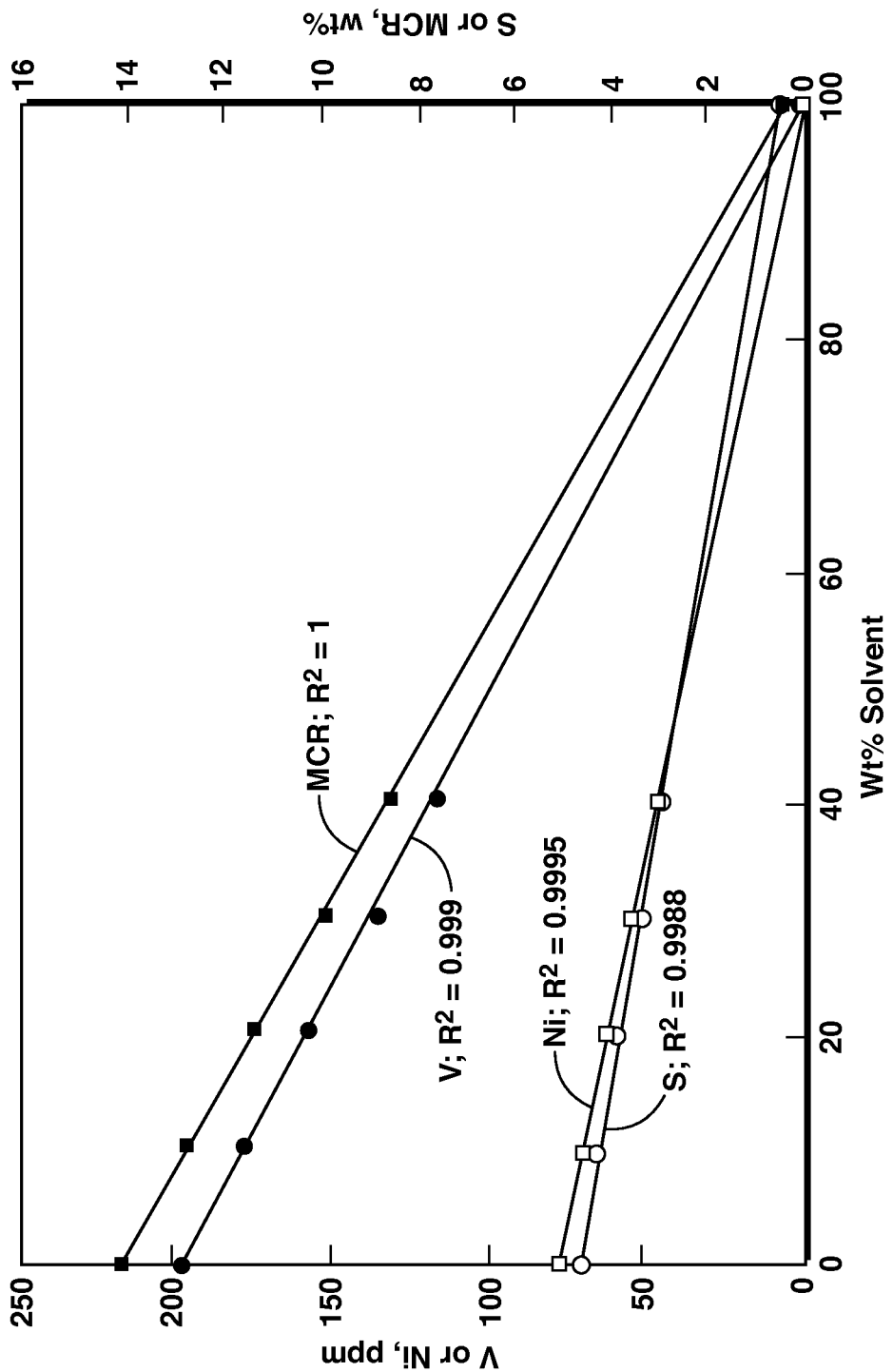
FIG. 6 is a diagram of test data illustrating the relationship between different native bitumen markers and the concentration of a solvent in a solvent/heavy oil blend.

FIG. 6 is a diagram of test data illustrating the relationship between different NBMs and the concentration of a solvent, such as 208, in a solvent/heavy oil blend, such as 210 and/or 216. More specifically, the amount of nickel (Ni) and vanadium (V), measured in parts per million on the left Y-axis, are plotted against the solvent concentration, in weight percent solvent, on the X-axis. In this particular example the solvent may be a gas plant condensate. $R^2$ in the plot indicates the correlation coefficient between the known and NBM-measured solvent concentration; an $R^2$ closer to 1 indicating an excellent fit. The resulting plots illustrate a substantially linear relationship between these NBMs and the concentration of a corresponding solvent in a blend. Similarly, the amount of sulfur (S) and micro-carbon residue (MCR), measured in parts per million on the right Y-axis, are plotted against the solvent concentration, in weight percent solvent, on the X-axis. The resulting plots also illustrate a substantially linear relationship between the two NBMs and the concentration of a corresponding solvent in a blend.

Figure 7:
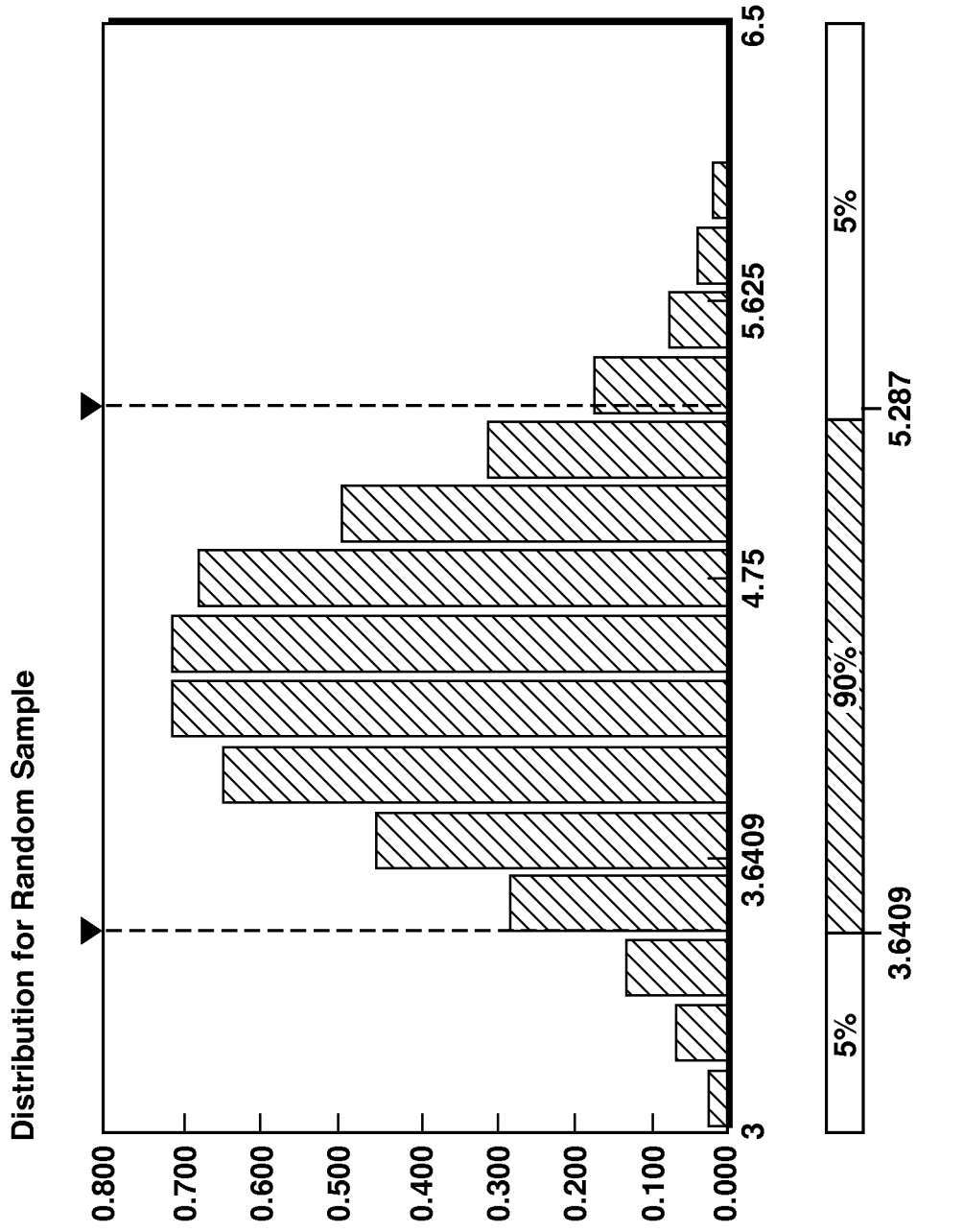
FIG. 7 is a simulation data plot illustrating the distribution of sulfur in bitumen generated by Latin-Hypercube sampling.

In practicing one or more embodiments of the present invention, one may encounter variation in bitumen NBM properties with time. If the variation is random, the effect on the cumulative solvent accounted for will generally be minimal, especially if the number of samples taken for NBM measurements is large. The number of samples needed to achieve certain accuracy may be estimated by performing a statistical simulation using known distribution in the variation of each NBM. The steps involved in the simulation may include:

(a) generating multiple samples with different values of each bitumen NBM using its known probability distribution and Monte-Carlo or Latin Hypercube sampling. Latin Hypercube sampling is preferred to Monte-Carlo sampling as the former requires fewer samples to reproduce the chosen distribution. An example of a distribution generated for bitumen sulfur using Latin Hypercube sampling is shown in FIG. 7.

(b) generating a "measured" blend NBM using a known recovery-aid solvent fraction and an appropriate blending model such as the model described in connection with method 100.

(c) adjusting the recovery-aid solvent fraction until the sum of squares of the differences between "measured" and predicted NBM calculated by using the blending model is minimized. A weighted regression, in which the weights are inversely proportional to the variance in the NBM may be used to improve estimation of the best-fit "analyzed" solvent fraction.

Figure 8A:
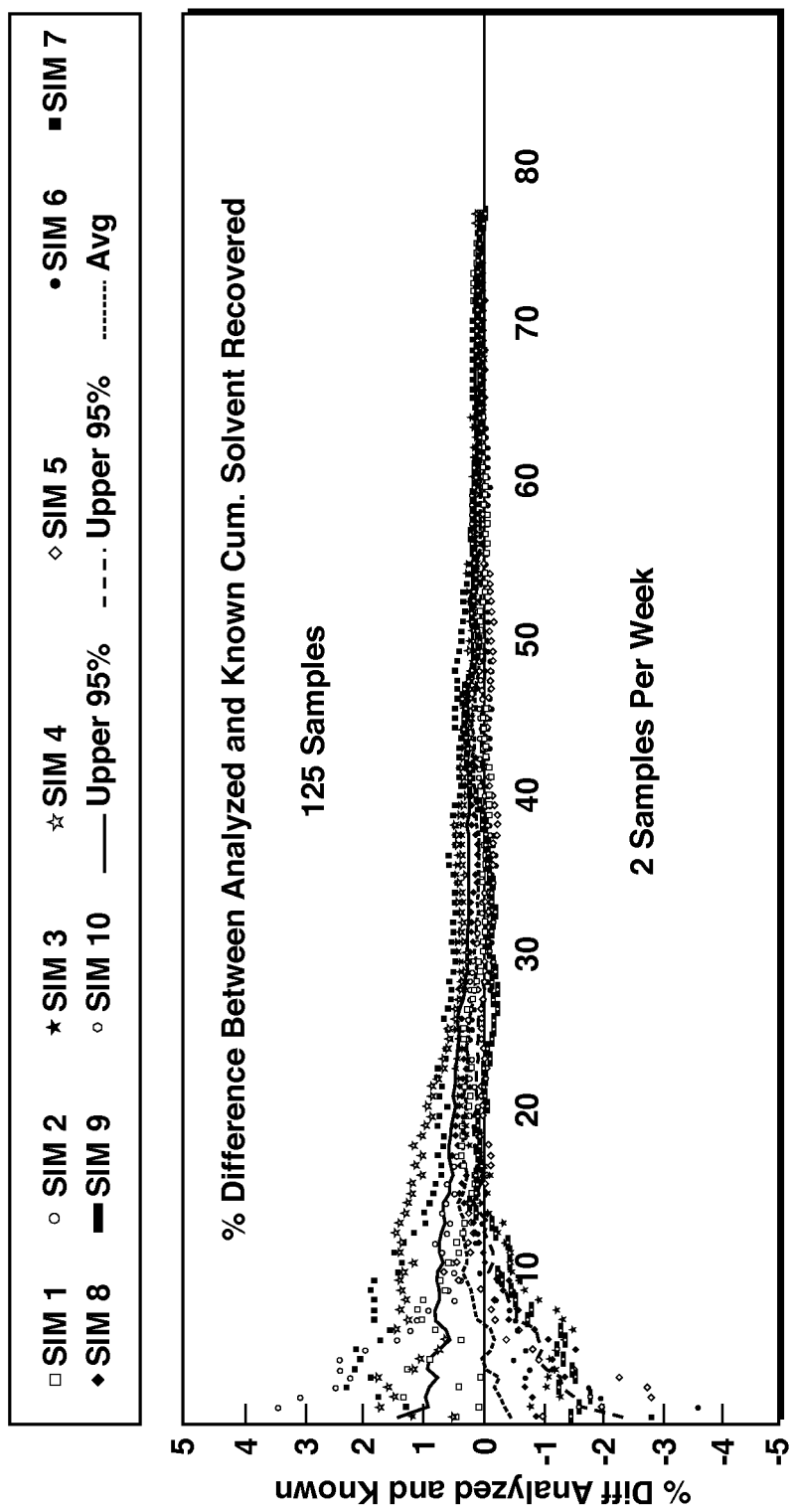
FIGS. 8(a-c) are simulation data plots illustrating that accuracy generally increases as the sample number increases.
Figure 8B:
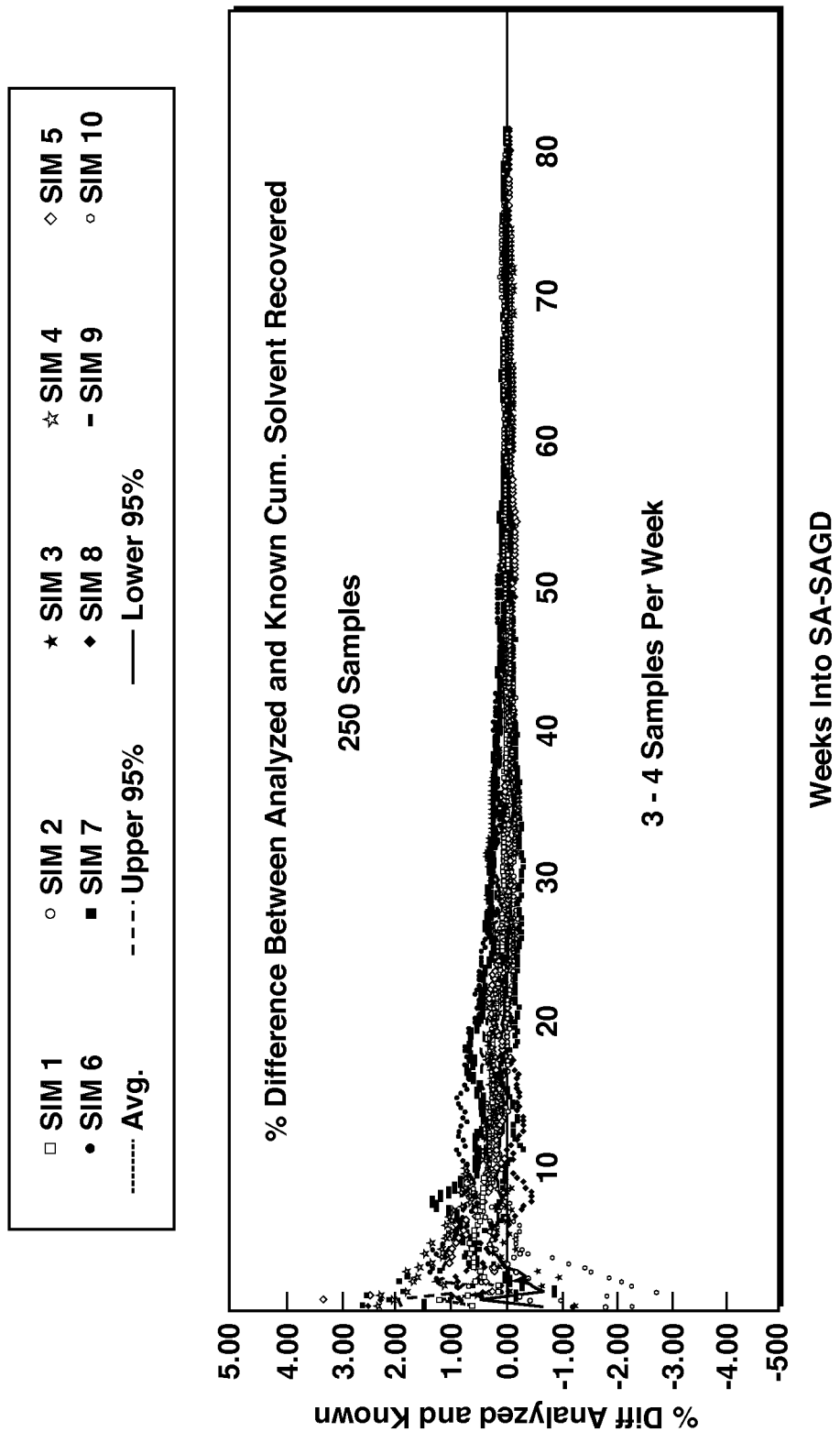
Figure 8C:
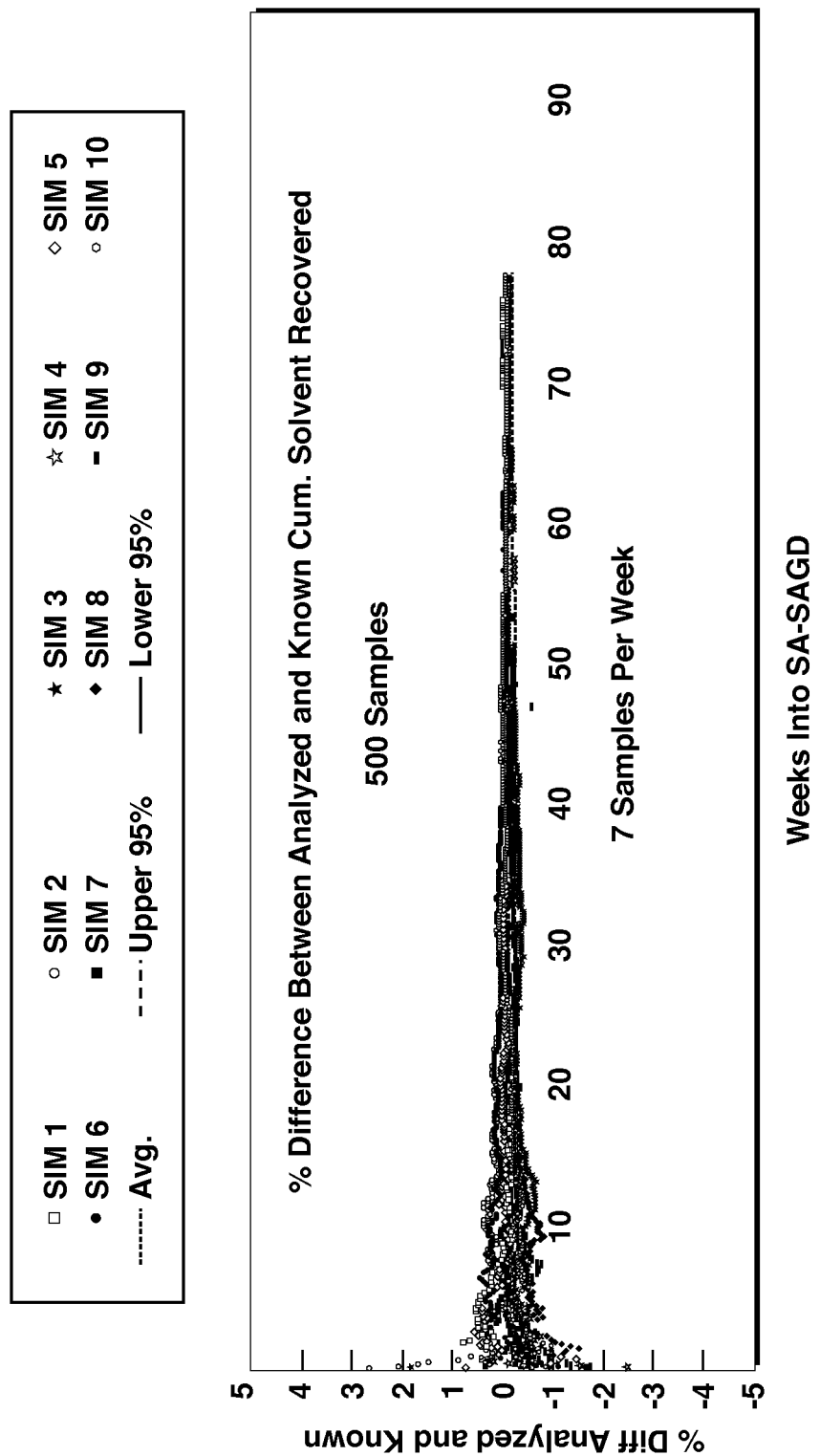

FIGS. 8(A-C) show the simulation results for 125 (~2 samples per week), 250 (~4 samples per week) and 500 (~7 samples per week) samples, respectively, for a typical SA-SAGD operation. As the sample number increases, the % difference between "analyzed" and known cumulative solvent volume decreases. These figures also suggest that the accuracy may be further improved through increased sampling at the early stages of production from a well.

For a given reservoir, the NBM variation in bitumen can be determined and taken into account in the solvent fraction determination by measuring the bitumen in the core samples from different parts of the reservoir.

In a typical SA-SAGD application, the NBM variation in bitumen may generally be handled by taking bitumen samples during the warm-up period of the process (when solvent typically is not injected or produced) and analyzing the bitumen for NBM.

In an SA-SAGD piloting, NBM variation in bitumen can be determined by taking samples from the portion of the test where only steam is injected and determining the NBM in the bitumen without the solvent.

Similarly, the variation in solvent NBM can be taken into account by taking samples of injected solvent at different times and adjusting the blending model accordingly.

As may be appreciated, then, the present invention represents an improvement in solvent surveillance for solvent-based heavy oil recovery processes. The present invention may be susceptible to various modifications and alternative forms, and the exemplary embodiments discussed above have been shown only by way of example. It should again be understood that the invention is not intended to be limited to the particular embodiments disclosed herein. Indeed, the present invention includes all alternatives, modifications, and equivalents falling within the true spirit and scope of the appended claims.

What is claimed is:

1. A method of solvent surveillance, comprising the steps of: (a) measuring an amount of a native bitumen marker (NBM) in heavy oil; (b) measuring an amount of the NBM in a recovery-aid solvent; (c) measuring an amount of the NBM in a blend, wherein the blend comprises the heavy oil and the recovery-aid solvent; (d) applying a blending model to determine a fraction of the recovery-aid solvent in the blend, wherein the blending model is at least partially described by formula: the fraction of the recovery-aid solvent in the blend= (NBMo-NBMb)/(NBMo-NBMras); wherein NBMo is the amount of the NBM in the heavy oil, NBMb is the amount of the NBM in the blend, NBMras is the amount of the NBM in the recovery-aid solvent; (e) generating an output that corresponds to the amount of recovery-aid solvent in the blend; and (f) adjusting at least one step in a solvent recovery process in response to the output.

2. The method of claim 1, wherein the fraction of the recovery-aid solvent and the amounts of the NBM are all measured in a unit selected from the group consisting of weight fraction, mole fraction, volume fraction, parts per million by volume, and parts per million by weight.

3. The method of claim 1 wherein the blend further comprises a separation-aid solvent and the method further includes the step of determining a fraction of the separation-aid solvent in the blend, wherein: the blending model is at least partially described on a separation-aid solvent free basis by formula: the fraction of the recovery-aid solvent in the blend=[NBMo-NBMb*(1/(1-SASFb)]/(NBMo-NBMras); NBMo is the amount of the NBM in the heavy oil; NBMb is the amount of the NBM in the blend; SASFb is the fraction of the separation-aid solvent in the blend; and NBMras is the amount of the NBM in the recovery-aid solvent.

4. The method of claim 1, wherein the NBM is a component that is substantially present in the heavy oil and substantially lacking in the recovery-aid solvent.

5. The method of claim 1, wherein the NBM is selected from the group consisting of sulfur (S), nickel (Ni), vanadium (V), chromium (Cr), micro-carbon residue (MCR), Conradson carbon residue (CCR), nC5-asphaltenes, nC6-asphaltenes and nC7-asphaltenes.

6. The method of claim 1, wherein the measurements are made using at least one of X-Ray Fluorescence analyzer, Inductively Coupled Plasma Emission Spectroscopy (ICPES), combustion fluorescence, ultraviolet fluorescence, solvent precipitation of asphaltenes, and pyrolysis in absence of oxygen.

7. The method of claim 1, wherein the blend is obtained using a solvent-based heavy oil production process selected from the group consisting of Expanding Solvent Steam Assisted Gravity Drainage ("ES-SAGD"), Solvent Assisted Steam Assisted Gravity Drainage ("SA-SAGD"), Liquid Addition to Steam for Enhanced Recovery ("LASER"), Vapor Extraction ("VAPEX"), Combined Vapor and Steam Recovery ("SAVEX"), Cyclic Solvent Process ("CSP"), Hot Solvent Process, and any combination thereof.

8. The method of claim 1 further comprising the step of recovering, in the solvent recovery process, at least a portion of the recovery-aid solvent from the blend.

9. The method of claim 8, wherein the solvent recovery process is selected from the group consisting of distillation, fractionation, evaporation, and any combination thereof.

10. The method of claim 1, wherein a plurality of NBMs are used to determine the fraction of the recovery-aid solvent.

11. The method of claim 1 further comprising the step of correlating the determined fraction of the recovery-aid solvent in the blend to an overall effectiveness of a solvent-based heavy oil production process, wherein the blend is generated during the solvent-based heavy oil production process.

12. The method of claim 11 further comprising the step of adjusting at least one step in the solvent-based heavy oil production process in response to the determined fraction of the recovery-aid solvent in the blend.

13. A heavy oil production method, comprising: injecting a recovery-aid solvent into a heavy oil formation to form an initial blend of the recovery-aid solvent and heavy oil; recovering the initial blend from a reservoir using a solvent-based production process; recovering, in a solvent recovery process, at least a portion of the recovery-aid solvent from the initial blend to form a partially recovered blend; and applying a solvent surveillance method to the partially recovered blend, the solvent surveillance method comprising: (a) measuring an amount of a native bitumen marker (NBM) in the heavy oil; (b) measuring an amount of the NBM in the recovery-aid solvent; (c) measuring an amount of the NBM in the partially recovered blend; and (d) applying a blending model to determine a fraction of the recovery-aid solvent in the partially recovered blend, wherein the blending model is at least partially described by formula: the fraction of the recovery-aid solvent in the partially recovered blend=(NBMo-NBMb)/(NBMo-NBMras); wherein NBMo is the amount of the NBM in the heavy oil, NBMb is the amount of the NBM in the partially recovered blend, NBMras is the amount of the NBM in the recovery-aid solvent.

14. The method of claim 13, wherein the fraction of the recovery-aid solvent and the amounts of the NBM are all measured in a unit selected from the group consisting of weight fraction, mole fraction, volume fraction, parts per million by volume, and parts per million by weight.

15. The method of claim 13, further comprising blending a separation-aid solvent with at least one of the initial blend and the partially recovered blend; and the solvent surveillance method further including determining a fraction of the separation-aid solvent in the partially recovered blend, wherein: the blending model is at least partially described by formula: the fraction of the recovery-aid solvent on a separation-aid solvent free basis in the partially recovered blend=[NBMo-NBMb*(1/(1-SASFb)]/(NBMo-NBMras); NBMo is the amount of the NBM in the heavy oil; NBMb is the amount of the NBM in the partially recovered blend; SASFb is the fraction of the separation-aid solvent in the partially recovered blend; and NBMras is the amount of the NBM in the recovery-aid solvent.

16. The method of claim 13, further comprising adjusting at least one step in the solvent recovery process in response to the determined fraction of the recovery-aid solvent in the partially recovered blend.

17. The method of claim 13 wherein a plurality of NBMs are used to determine the fraction of the recovery-aid solvent.

18. The method of claim 13, wherein the NBM is an element that is substantially present in the heavy oil and substantially lacking in the recovery-aid solvent.

19. The method of claim 13, wherein the NBM is selected from the group consisting of sulfur (S), nickel (Ni), vanadium (V), chromium (Cr), micro-carbon residue (MCR), Conradson carbon residue (CCR), nC5-asphaltenes, nC6-asphaltenes and nC7-asphaltenes.

20. The method of claim 13, wherein the measurements are made using at least one of an X-Ray Fluorescence analyzer, an Inductively Coupled Plasma Emission Spectroscopy (ICPES), combustion fluorescence, ultraviolet fluorescence, solvent precipitation of asphaltenes, and pyrolysis in absence of oxygen.

21. The method of claim 13, wherein the solvent-based production process is selected from the group consisting of Expanding Solvent Steam Assisted Gravity Drainage ("ES-SAGD"), Solvent Assisted Steam Assisted Gravity Drainage ("SA-SAGD"), Liquid Addition to Steam for Enhancing Recovery ("LASER"), Vapor Extraction (VAPEX), Combined Vapor and Steam Recovery ("SAVEX"), Cyclic Solvent Process, Hot Solvent Process, and any combination thereof.

22. The method of claim 13, wherein the solvent recovery process is selected from the group consisting of distillation, fractionation, evaporation, membrane separation, and any combination thereof.

23. The method of 13 further comprising the step of relating the fraction of the recovery-aid solvent to an overall effectiveness of the solvent recovery process.

24. The method of claim 13 wherein the solvent surveillance method is applied to a plurality of samples of the partially recovered blend to minimize an effect of variations in concentration of the NBM in at least one of the heavy oil and the recovery-aid solvent.

25. The method of claim 13 further comprising adjusting at least one step in the solvent-based production process in response to the determined fraction of the recovery-aid solvent in the partially recovered blend.

* * * * *